(12) United States Patent
Klemm et al.

(10) Patent No.: US 8,256,047 B2
(45) Date of Patent: Sep. 4, 2012

(54) COMBINATION TREATMENT DEVICE AND AN ANTERIOR SUPPORT DEVICE

(76) Inventors: Kurt W. Klemm, Rhinelander, WI (US); Gregory J. Books, Omro, WI (US); Greg Macheel, Rancho Palos Verdes, CA (US)

( * ) Notice: Subject to any disclaimer, the term of this patent is extended or adjusted under 35 U.S.C. 154(b) by 294 days.

(21) Appl. No.: 12/800,619

(22) Filed: May 18, 2010

(65) Prior Publication Data

US 2010/0293719 A1 Nov. 25, 2010

Related U.S. Application Data

(63) Continuation-in-part of application No. 12/080,607, filed on Apr. 3, 2008, now abandoned.

(51) Int. Cl.
*A47B 7/00* (2006.01)
(52) U.S. Cl. ............................. 5/621; 5/630; 128/845
(58) Field of Classification Search ........ 5/612, 621–624, 5/630, 646, 648, 507.1, 658; 108/49; 128/845, 128/846, 869, 870, 878, 882; 248/118, 161
See application file for complete search history.

(56) References Cited

U.S. PATENT DOCUMENTS

| | | |
|---|---|---|
| 135,435 A | 2/1873 | Lyon |
| 1,134,720 A | 4/1915 | Bradley |
| 2,038,806 A | 4/1936 | Sellar |
| 2,519,771 A | 8/1950 | Lacore |
| 3,020,909 A | 2/1962 | Stevens |
| 3,216,767 A | 11/1965 | Lutfy |
| 3,848,838 A | 11/1974 | Thomas |
| 3,897,778 A | 8/1975 | Forbes-Robinson et al. |
| 3,977,645 A | 8/1976 | Deely |
| 4,397,374 A | 8/1983 | Rumage |
| 4,431,329 A | 2/1984 | Baitella |
| 4,549,540 A | 10/1985 | Caspari et al. |

(Continued)

FOREIGN PATENT DOCUMENTS

WO 8606940 12/1986

(Continued)

OTHER PUBLICATIONS

AliMed, Medical and Ergonomic Products for Healthcare, Business and Home, Internet, www.alimed.com/ProductDetail, date printed Dec. 4, 2006, one page.

(Continued)

*Primary Examiner* — Robert G Santos
*Assistant Examiner* — Nicholas Polito
(74) *Attorney, Agent, or Firm* — Thomas J. Connelly; Wilhelm Law, S.C.

(57) ABSTRACT

A combination of a treatment device and an anterior support device is disclosed. The combination includes a treatment device having an edge and an attachment member movably secured thereto and an anterior support device having an elongated member which interacts with the attachment member. The anterior support device has first and second pivotable connectors, one being secured to the elongated member and the other to a padded rest. The anterior support device also includes first and second movable rods secured to the first and second pivotable connectors. A second end of the first movable rod is rotatably connected to a second end of the second movable rod and an actuating mechanism is connected to both of the second ends of the rods. The actuating mechanism enables the first and second rods to be locked in a set position to maintain the padded rest in a desired orientation relative to the treatment device.

20 Claims, 8 Drawing Sheets

U.S. PATENT DOCUMENTS

| | | | |
|---|---|---|---|
| 4,579,324 | A | 4/1986 | McConnell |
| 4,702,465 | A | 10/1987 | McConnell |
| 4,727,958 | A | 3/1988 | Botello |
| 4,858,903 | A | 8/1989 | Tari et al. |
| 4,886,258 | A | 12/1989 | Scott |
| 4,917,343 | A | 4/1990 | Wainscott |
| 5,118,062 | A | 6/1992 | Archambault |
| 5,281,001 | A | 1/1994 | Bergsten et al. |
| 5,295,728 | A | 3/1994 | Schaevitz |
| 5,390,383 | A | 2/1995 | Carn |
| 5,545,177 | A | 8/1996 | Coseo |
| 5,575,027 | A | 11/1996 | Mueller |
| 5,582,379 | A | 12/1996 | Keselman et al. |
| 5,775,334 | A | 7/1998 | Lamb et al. |
| 5,887,948 | A | 3/1999 | Hannes |
| 5,918,330 | A | 7/1999 | Navarro et al. |
| 5,961,085 | A | 10/1999 | Navarro et al. |
| 5,961,512 | A | 10/1999 | Purnell |
| 6,102,344 | A | 8/2000 | Kasvin et al. |
| 6,138,970 | A | 10/2000 | Sohrt et al. |
| 6,210,325 | B1 * | 4/2001 | Bartie et al. ............... 600/229 |
| 6,267,336 | B1 | 7/2001 | Ruckstadter |
| 6,298,507 | B1 | 10/2001 | Clyburn |
| 6,309,329 | B2 | 10/2001 | Conner |
| 6,435,186 | B1 | 8/2002 | Klemm |
| 6,553,918 | B2 | 4/2003 | Bieza |
| 6,554,238 | B1 | 4/2003 | Hibberd |
| 6,622,324 | B2 | 9/2003 | VanSteenburg et al. |
| 6,629,944 | B2 * | 10/2003 | Smart ............... 602/36 |
| 6,644,748 | B2 | 11/2003 | Tholkes et al. |
| 6,708,935 | B2 | 3/2004 | Smeed |
| 6,820,621 | B2 | 11/2004 | DeMayo |
| 6,941,951 | B2 | 9/2005 | Hubert et al. |
| 7,422,016 | B2 | 9/2008 | Klemm |
| 7,624,737 | B2 | 12/2009 | Klemm |
| 2002/0158492 | A1 | 10/2002 | Ko et al. |
| 2005/0015879 | A1 | 1/2005 | Cuschieri et al. |
| 2008/0054698 | A1 | 3/2008 | Klemm et al. |

FOREIGN PATENT DOCUMENTS

| | | |
|---|---|---|
| WO | 03017859 | 3/2003 |
| WO | 2005023072 | 3/2005 |

OTHER PUBLICATIONS

Dentech Corporation, Dentech Advance Stools, Internet, wwwdentechcorp.com/products/stools.html, date printed Apr. 4, 2007, two pages.

DK&E Technology, Kobo Chair by DK&E Technology, Internet, www.kobochair.com/products.html, date printed Mar. 19, 2007, one page.

DK&E DSD Diamond Burs, Kobo Chair, Internet, www.kobochair.com/iframes.productinfo.html, date printed Oct. 13, 2005, one page.

Office Organix, Office Organix, Advanced Ergonomics @ Internet Prices, Internet, www.officeorganix.com/NPAstool.html, date printed Mar. 19, 2007, five pages.

Takara Belmont, Takara Belmont, Contact Us, Internet, www.takarabelmont.com/contact/, date printed Sep. 25, 2007, two pages.

Takara Belmont, Takara Belmont, Medical, DR-220, DG-310, DG-700, Internet, www.takarabelmont.co.jp/webcore/hp/page0000007001 . . . , date printed Sep. 25, 2007, three pages.

Midmark Company, Midmark Company History, Internet, www.midmark.com, date printed Sep. 25, 2007, five pages.

TENET Medical Engineering, TENET Medical Engineering, Innovative Orthopedic Positioning Products, The SPIDER, Internet, www.tenetmedical.com/spider.html, date printed Jul. 2, 2007, two pages.

Skytron, Skytron Body Support Accessories, Internet, www.skytron.us/bodysupp_acc1.htm, date printed Apr. 26, 2007, one page.

* cited by examiner

COMBINATION TREATMENT DEVICE AND AN ANTERIOR SUPPORT DEVICE

RELATED U.S. APPLICATION DATA

This application is a Continuation-In-Part application of U.S. Ser. No. 12/080,607 filed Apr. 3, 2008.

FIELD OF THE INVENTION

This invention relates to a combination of a treatment device and an anterior support device upon which a provider, such as a doctor, an anesthesiologist, a veterinarian, etc. can lean his or her torso against while administering to a person or animal positioned on the treatment device.

BACKGROUND OF THE INVENTION

Today, many medical practitioners, including but not limited to surgeons, anesthesiologists, oral surgeons, neurosurgeons, operating room technicians, first assistants, doctors, nurses, veterinarians, chiropractors, etc., are required to lean forward or bend over a patient or animal that is being operated on, examined or administered to. In addition, people in other occupations, including but not limited to: a massage therapist, a tattoo artist, a researcher in a laboratory, an assembly line person, a person who work over a dissection table, a drafting table, a lab bench, at a hobby station, a pottery workstations, at a work bench, at a manicure/pedicure workstation, at a sorting table, at an assembly line table/work bench, find themselves in a leaning forward or in a bent over position. The amount of time required to examine, administer to, or perform surgery on a person or animal can vary and some procedures require several hours to complete. In addition, many surgeons, anesthesiologists, oral surgeons, operating room technicians, first assistants, nurses, veterinarians, etc. perform several surgical or medical procedures in a day. At some of the other tasks mentioned above, a person may be required to bend forward throughout most of the work day. Such repetitive and/or prolonged activity over a period of time can be a major cause of back, neck, shoulder, and/or arm pain, muscle soreness and dysfunction. Affected individuals, after awhile, can no longer endure such pain and suffering and are forced to drastically modify their work areas or discontinue performing their required tasks.

To alleviate such body pain and discomfort, some individuals turn to physical therapy, medical intervention or exercise. Others attempt to support their backs while performing their required tasks by using braces and/or cushions that are intended to support their spine in an anatomically erect position. These devices are generally designed to support the individual from the rear and thus are not the most effective for individuals who must be in a forward leaning or flexed position, as a fundamental part of their work.

As our population ages, many older adults are requiring various forms of surgery or other medical procedures. This in turn has placed added pressure on surgeons and other operating room personnel to work longer hours and perform more surgeries than ever before. Furthermore, as our population has increased, the number of pets being kept has also increased and a higher percentage of such pets are also living longer. This has placed added pressure on veterinarians and their surgical assistances to also work longer hours and perform more surgeries than ever before.

In order to prolong the ability of surgeons, anesthesiologists, oral surgeons, operating room technicians, first assistants, doctors, nurses, veterinarians, chiropractors, etc., to practice their specialty, there is a need for an anterior rest upon which they can lean or rest their torsos so as to reduce and/or eliminate body pain and soreness.

Now a combination of a treatment device and an anterior support device has been invented that can do just that.

SUMMARY OF THE INVENTION

Briefly, this invention relates to a combination which includes a treatment device having a longitudinal central axis and an edge. An attachment member is movably secured to the edge. The attachment member has an aperture formed therethrough and a tightening device which interacts with the aperture. The combination also includes an anterior support device having an elongated member sized and configured to be inserted into the aperture and is capable of being retained in a predetermined position by the tightening device. The anterior support device also includes an adapter secured to the elongated member, a first pivotable connector secured to the adapter and a first movable rod. The first movable rod has a first end and a second end with the first end engaging the first pivotable connector and capable of pivoting thereabout. The anterior support device further including a padded rest against which a user can lean his or her torso, a second pivotable connector secured to the padded rest, and a second movable rod. The second movable rod has a first end and a second end with the first end engaging the second pivotable connector and capable of pivoting thereabout. The second end of the second movable rod is rotatably connected to the second end of the first movable rod. An actuating mechanism is connected to the first and second movable rods and enables the first and second movable rods to be locked in a set position to maintain the padded rest in a desired orientation relative to the treatment device.

In another embodiment, a combination is disclosed which includes a treatment device and an anterior support device. The treatment device has a planar surface with a longitudinal central axis, a pair of edges and a pair of rails each secured to one of the rails. An attachment member is movable along one of the rails and is capable of being secured at a desired position. The attachment member has an aperture formed therethrough and a tightening device which interacts with the aperture. The anterior support device includes an elongated member sized and configured to be inserted into the aperture and is capable of being retained in a predetermined position by the tightening device. The anterior support device also includes an adapter secured to the elongated member, a first pivotable connector secured to the adapter, and a first movable rod. The first movable rod has a first end and a second end with the first end engaging the first pivotable connector and capable of pivoting thereabout. The anterior support device further includes a padded rest against which a user can lean his or her torso, a second pivotable connector secured to the padded rest, and a second movable rod. The second movable rod has a first end and a second end with the first end engaging the second pivotable connector and being capable of pivoting thereabout. The second end of the first movable rod is rotatably connected to the second end of the second movable rod. The anterior support device also has an actuating mechanism connected to the first and second movable rods which enables the first and second rods to be locked in a set position to maintain the padded rest in a desired orientation relative to the treatment device.

The general object of this invention is to provide a combination treatment device and an anterior support device. A more specific object of this invention is to provide an anterior support device upon which a provider can lean his or her torso against while administering to a person or animal positioned on the treatment device.

Another object of this invention is to provide a combination treatment device and an anterior support device wherein the anterior support can be easily mounted to the treatment device.

A further object of this invention is to provide a combination treatment device and two anterior support devices wherein each of the anterior support devices is secured to the same edge of the treatment device.

Still another object of this invention is to provide a combination treatment device and two anterior support devices wherein each of the anterior support devices is secured to an opposite edge of the treatment device.

Still further, an object of this invention is to provide a combination treatment device and an anterior support wherein the height and orientation of the anterior support device can be quickly and easily adjusted.

Other objects and advantages of the present invention will become more apparent to those skilled in the art in view of the following description and the accompanying drawings.

DETAILED DESCRIPTION OF THE INVENTION

Figure 1:
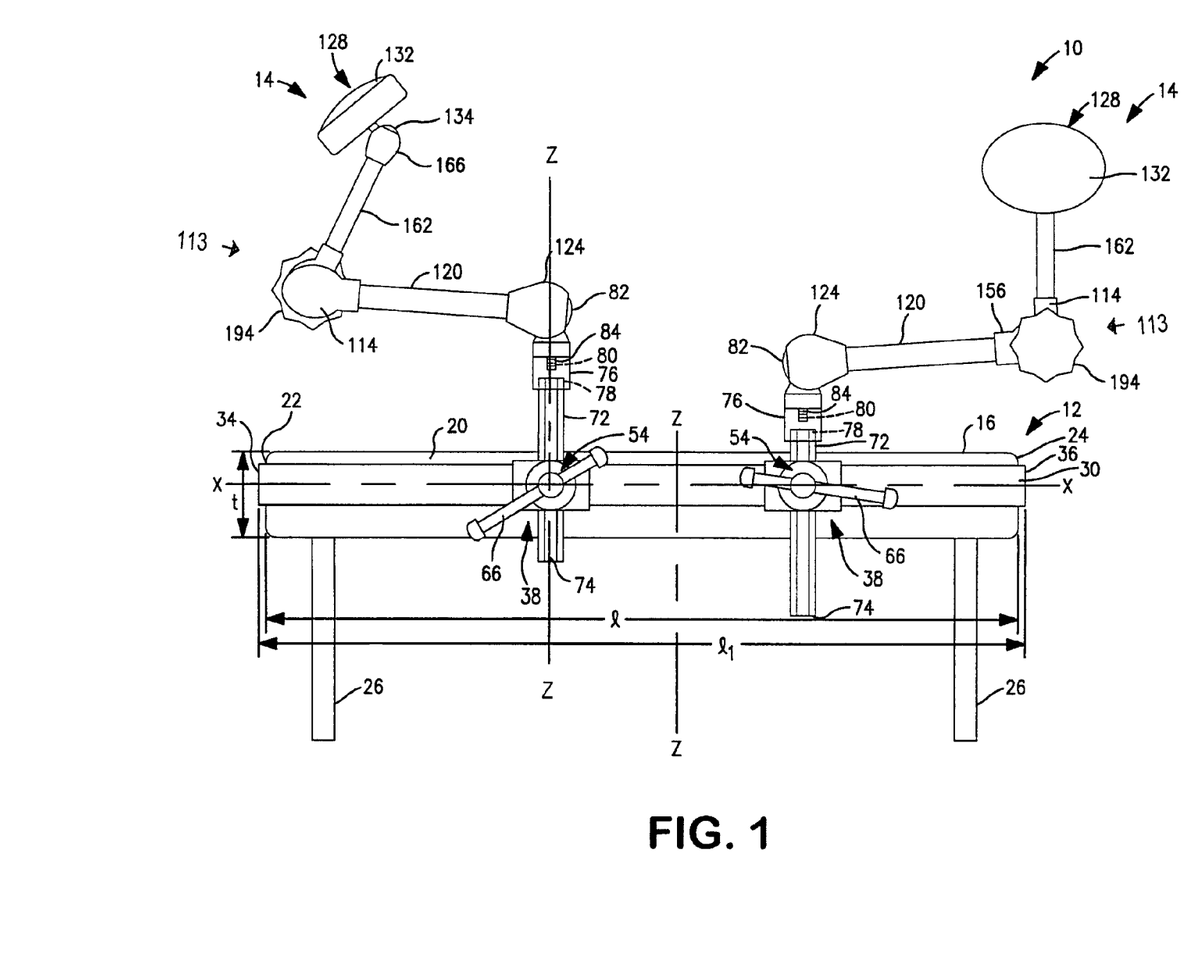
FIG. 1 is a side elevation view of a combination treatment device having a pair of attachment members secured to an edge thereof and each attachment member having an anterior support device secured thereto.

Referring to FIG. 1, a combination 10 is shown which includes a treatment device 12 and at least one anterior support device 14. The treatment device 12 can be a table, a chair, a surgical table, a work bench, an assembly line, a conveyor belt or any other structure of sufficient size and shape to support a person, an animal, or one or more objects. The objects can vary in size, shape and weight. In FIG. 1, the treatment device 12 is depicted as a surgical table having two anterior support devices 14 secured thereto. Each anterior support device 14 provides a rest upon which a provider, such as a doctor, an anesthesiologist, a veterinarian, etc., or a person working at a task in a forward leaning or in a flex position, can lean his or her torso against while performing surgery, doing an examination, administering to a person or animal positioned on the treatment device 12 or performing some other task.

Figure 2:
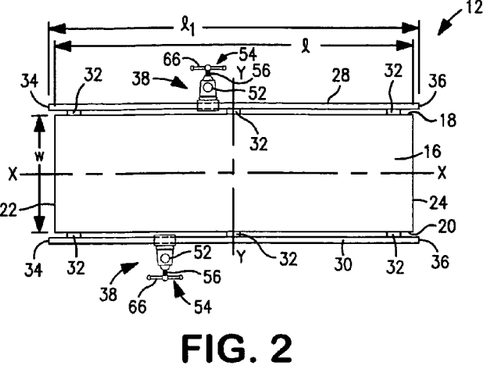
FIG. 2 is a top view of a treatment device having a longitudinal central axis X-X, a pair of rails secured to the opposite sides of the treatment device, and an attachment member movably attached to each of the pair of rails.
Figure 3:
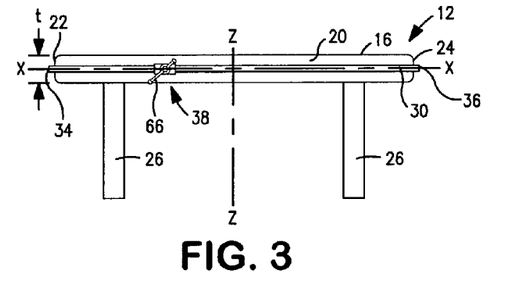
FIG. 3 is a front view of the treatment device shown in FIG. 2 depicting one of the attachment members and two of the four legs of the treatment device.
Figure 4:
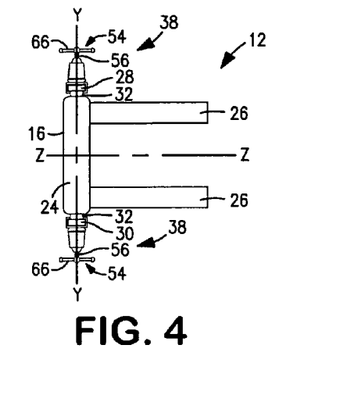
FIG. 4 is a side view of the treatment device shown in FIG. 2 depicting the two attachment members and two of the four legs of the treatment device.

Referring to FIGS. 1-2, the treatment device 12 has a major surface 16 with a longitudinal central axis X-X, a traverse central axis Y-Y, see FIG. 2, and a vertical central axis Z-Z. The major surface 16 is depicted as being flat or planar in configuration but it could have some other geometrical configuration as well. For example, the major surface 16 could be concave or convex relative to the longitudinal central axis X-X. The treatment device 12 has a length l, a width w, see FIG. 2, and a thickness t. The length l is measured parallel to the longitudinal central axis X-X, the width w is measured parallel to the transverse central axis Y-Y and the thickness t is measured parallel to the vertical central axis Z-Z. The treatment device 12 also has a first edge 18, see FIG. 2, and an oppositely aligned second edge 20. The treatment device 12 also has a first end 22 and an oppositely aligned second end 24. As depicted, the first and second edges, 18 and 20 respectively, are aligned perpendicular to the first and second ends, 22 and 24 respectively. The major surface 16 of the treatment device 12 is depicted having a rectangular configuration, although it could have some other geometrical shape, if desired. For example, the major surface 16 could be a square, an oval shape, a circle, etc. or could be asymmetrical in configuration.

It should be understood that the term "treatment device" can include a work bench or a work station where one or more objects are either positioned or are being conveyed and a person performs some sort of work on such objects. The work may be sorting one object from another, adding a component to an object, removing a component from an object, manipulating an object, etc. The term "treatment device" will also include "surgical chairs" such as those manufactured and sold by Takara Belmont Corporation having an office at 3010 D Woodcreek Drive, Downers Grove, Ill. 60515. "Surgical chairs" are also manufactured and sold by Midmark Corporation having an office at 60 Vista Drive, P.O. BOX 286, Versailles, Ohio 45380-0286. For purposes of describing the invention, the term "treatment device" will include any kind of table or chair used in the medical, dental or any other line of work.

Figure 5:
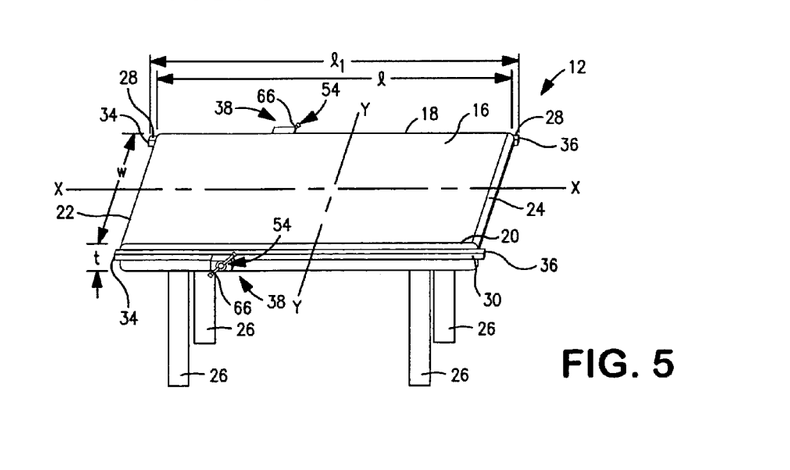
FIG. 5 is a perspective view of the treatment device shown in FIG. 2 depicting the two attachment members and all four legs.
Figure 6:
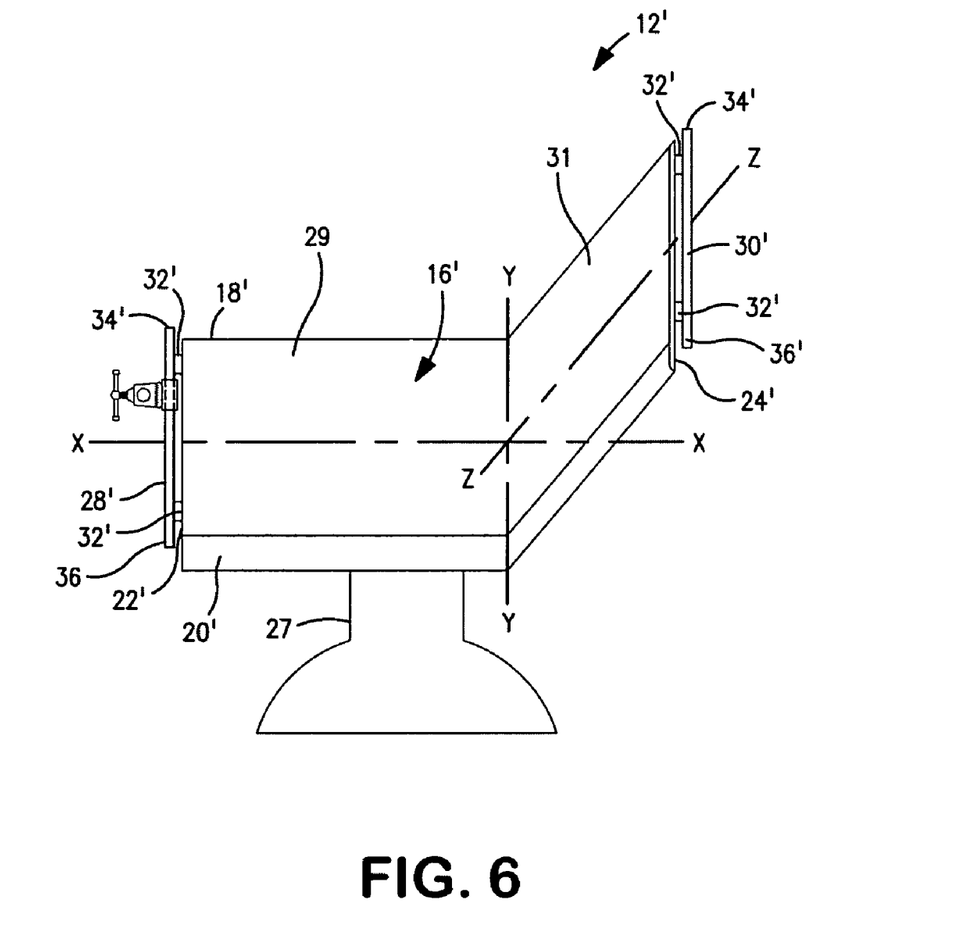
FIG. 6 is an alternative view of a treatment device wherein a portion of it can be manipulated into an upright arrangement and the treatment device has a pedestal base.

Referring to FIG. 5, the treatment device 12 has four legs 26 aligned perpendicular to the major surface 16. A greater number of legs 26 can be utilized, if desired. Alternatively, as shown in FIG. 6, a treatment device 12' having a major surface 16', a pair of oppositely aligned edges 18' and 20' and a pair of oppositely aligned ends 22' and 24' can be supported by a pedestal 27 instead of by a plurality of legs 26. The pedestal 27 should be of sufficient strength and structure to support the major surface 16'.

Referring again to FIG. 5, when the treatment device 12 has four legs 26, the legs 26 can be spaced apart from one another. The four legs 26 are shown being arranged as two pairs of legs 26. One of the two pairs of the legs 26 is positioned adjacent to the first end 22 and the other pair of legs 26 is positioned adjacent to the second end 24. The four legs 26 should be of sufficient length to raise the major surface 16 to a desired working height of the provider, i.e. doctor, etc. If desired, the four legs 26 can contain or be equipped with a hydraulic, pneumatic or telescoping mechanism (not shown) to raise and/or lower the height of the treatment table 12 to a desired level.

The treatment device 12 or 12' can be constructed out of a variety of materials. Such materials include, but not limited to: stainless steel, steel, aluminum, metal, a ferrous metal, a metal alloy, wood, a composite material, a thermoplastic material, a plastic material, etc. One company that manufactures stainless steel products for the hospitality and catering industries is Skytron—Cape Stainless having a mailing address of P.O. Box 250, Eppindust, 7475, Cape Town, South Africa.

Referring to FIGS. 2-5, the treatment device 12 also has a pair of rails 28 and 30 each secured to one of the first and second edges, 18 and 20 respectively, by a plurality of support members 32. It should be understood that a rail 28 or 30 can alternatively be attached to one or both ends 22 and 24, if desired. In FIG. 6, a pair of rails 28' and 30' are secured to the ends, 22' and 24' respectively, via support members 32'.

Referring again to FIG. 2, three support members 32 are used to secure the rail 28 to the first edge 18 and three support members 32 are used to secure the rail 30 to the second edge 20. However, it should be understood that a fewer or a greater number of support members 32 can be utilized. The pair of rails 28 and 30, and the support members 32, can be constructed out of the same material or out of a different material than the treatment device 12. Each of the pair of rails 28 and 30 extends along the length l of the treatment device 12. Each of the pair of rails 28 and 30 is shown having a length $l_1$ which is greater than the length l of the treatment table 12. However, each of the rails 28 and 30 can have a length $l_1$ which is equal to or less than the length l of the treatment table 12. Each of the pair of rails 28 and 30 has a first end 34 and a second end 36, see FIGS. 2, 3 and 5, and each of the first and second ends, 34 and 36 respectively, extend beyond the respective first and second ends, 22 and 24 respectively, of the treatment device 12. The amount that the first and second ends, 34 and 36 respectively, extend beyond the respective first and second ends, 22 and 24 respectively, of the treatment device 12 can vary but normally each of the first and second ends, 34 and 36 respectively, extends from between about 0.1 inches to about 2 inches beyond the respective first and second ends, 22 or 24 of the treatment device 12. Desirably, each of the first and second ends, 34 and 36 respectively, extends from between about 0.25 inches to about 1.5 inches beyond the respective first and second ends 22 or 24 of the treatment device 12. More desirably, each of the first and second ends, 34 and 36 respectively, extends from between about 0.5 inches to about 1 inch beyond the respective first and second ends 22 or 24 of the treatment device 12. Likewise, in FIG. 6, each of the rails 28' and 30' has a first end 34' and a second end 36' which extend beyond the first and second edges 18' and 20' of the treatment device 12'. The amount that the first and second ends, 34' and 36' respectively, extend beyond the respective first and second edges, 18' and 20' respectively, of the treatment device 12' can vary as explained above for the treatment device 12.

The first and second ends, 34 and 36 respectively, of the pair of rails 28 and 30 can each extend outward an equal distance from the first end 22 or second end 24 of the treatment device 12. Alternatively, the first end 34 of each of the pair of rails 28 and 30 can extend a greater or lesser distance from the first end 22 of the treatment device 12 than the second end 36 of the pair of rails 28 and 30 extend from the second end 24 of the treatment device 12. The same hold true for the first and second ends, 34' and 36' respectively, of the pair of rails 28' and 30' of the treatment device 12 depicted in FIG. 6.

Referring to FIG. 6, a first portion 29 of the treatment device 12' is capable of folding, angling, pivoting, tilting or moving relative to a second portion 31 to create a treatment device 12' that can be transformed from a flat table arrangement to a chair like configuration. In FIG. 6, the first and second portions 29 and 31 can fold, angle, pivot or move along the transverse central axis Y-Y. The second portion 31 can be angled from between 0 to about 90 degrees relative to the first portion 29. This ability to move the second portion 31 relative to the first portion 29 enables a patient to lay flat on the treatment device 12' or be moved or manipulated into a quasi seating position or into a seating position. This versatility may assist the provider in examining or treating the patient.

Figure 7:
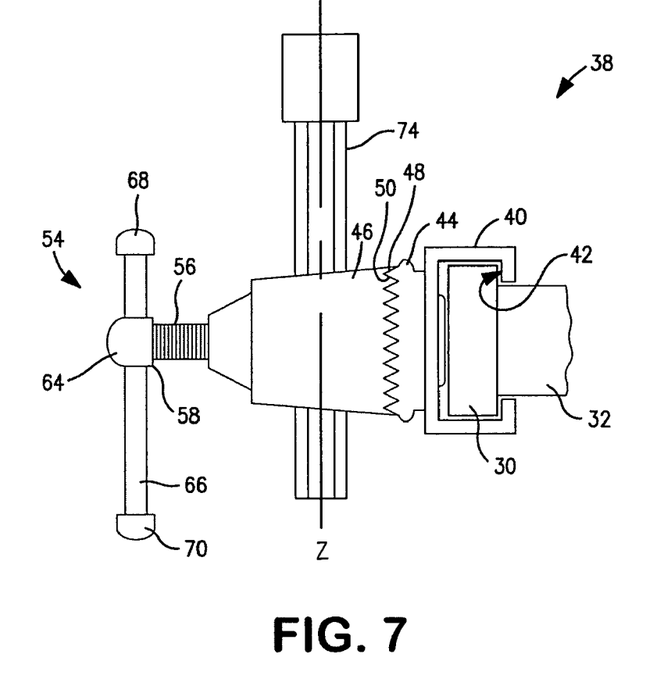
FIG. 7 is a side view of an attachment member secured to an edge of the treatment device and having an elongated member of an anterior support device secured thereto.
Figure 8:
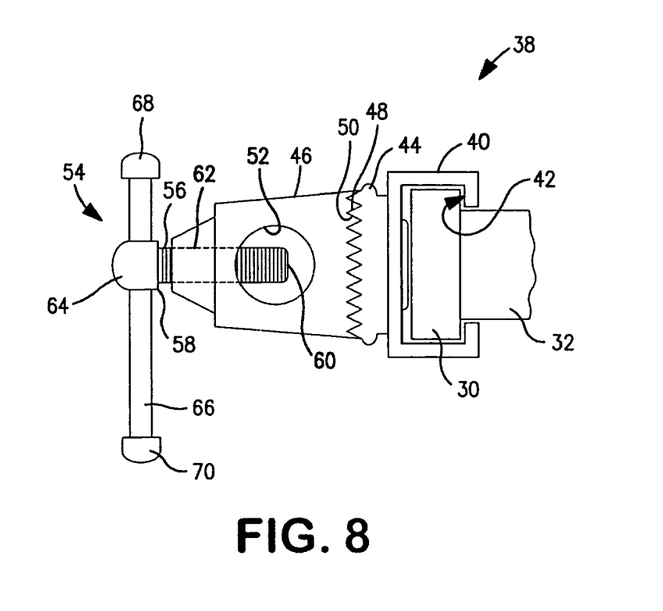
FIG. 8 is a top view of the attachment member shown in FIG. 7 without the elongated member of the anterior support device so as to expose the aperture formed in the attachment member.

Referring to FIGS. 7 and 8, the combination 10 also includes an attachment member 38. The attachment member 38 can be a clamp, formed in various shapes and sizes. Desirably, the attachment member 38 is a Clark Socket Clamp when used with a medical or surgical table or chair. A "Clark Socket Clamp" is a unique clamp commonly attached to a medical or surgical table and is well known to those skilled in making and selling medical and surgical equipment. The attachment member 38 is movably secured to one of the rails 28 or 30, 28' or 30', or to one of the edges 18 or 20, or 18' or 20' of the treatment device 12 or 12'. For example, the attachment member 38 can be movable along one of the pair of rails 28 or 30, or 28' or 30' by a bracket 40 having a generally C-shaped channel 42 formed therein. The generally C-shaped channel 42 is sized and configured to closely match the height and thickness dimensions of the rail 28 or 30, or 28' or 30' along which it can slide. This close tolerance will allow the attachment member 38 to slide horizontally back and forth on the rail 28 or 30, or 28' or 30' to which it is fitted. The bracket 40 will also prevent the attachment member 38 from being pulled outward, parallel to the transverse central axis Y-Y, and away from the respective rail 28 or 30, or 28' or 30' to which it is mounted.

In order to initially position the attachment member 38 on one of the pair of rails 28 or 30, or 28' or 30', the bracket 40 is slid onto either the first end 34 or 34' or the second end 36 or 36' of one of the rails 28 or 30, or 28' or 30' respectively. The attachment member 38 can be positioned anywhere along the length l of the treatment device 12 or 12'. It should be understood that one could mount a single attachment member 38 onto the treatment device 12 or 12'. Alternatively, two or more attachment members 38, 38 can be utilized at the same time. In FIG. 2, two attachment members 38, 38 are depicted, one being moveably mounted to the rail 28 and the second being moveably mounted to the rail 30. Optionally, two or more attachment members 38 can be moveably mounted onto one or both of the pair of the rails 28 and 30.

Each attachment member 38 has a first body member 44 and a second body member 46. The first and second body members, 44 and 46 respectively, each have a round or circular cross-sectional configuration; although any other geometrical shape can be utilized. The first body member 44 is securely attached to the bracket 40, such as by a weld, machine screws, dowel pins, etc., or it can be casted or formed from a unitary piece of material. The first body member 44 has a serrated portion 48. By "serrated" it is meant an area of small sharp projections resembling the teeth of a saw; having a saw-toothed edge or margin notched with tooth-like projections.

In FIG. 7, the serrated portion 48 is a circular edge. The second body member 46 also has a serrated portion 50 which is sized and configured to mate with the serrated portion 48 of the first body member 44. The serrated portions 48 and 50 permit the second body member 46 to be angularly positioned relative to the first body member 44. In order to rotate the second body member 46 relative to the first body member 44, one simply separates the two body members 44 and 46 and then rotates one relative to the other. After such rotation, the first and second body members, 44 and 46 respectively, are brought back into contact and engagement with one another. Although not shown, a screw, a spring, or some other mechanical device can be used to bias or urge the second body member 46 into physical contact with the first body member 44. One skilled in the art will understand that the serrated portions 48 and 50 allow one to vary the angular orientation of the second body member 46 relative to the first body member 44. For example, the first body member 44 can be rotated from between 0 to 360 degrees relative to the second body member 46 or relative to the vertical central axis Z-Z.

Referring to FIG. 8, the second body member 46 has an aperture 52 formed therethrough. The aperture 52 is depicted as having an elliptical cross-section although any other geometrical shape can be utilized, if desired. For example, the aperture 52 could have a round or circular cross-section, a polygon cross-section such as a triangular cross-section, a square cross-section, a pentagon cross-section, a hexagonal cross-section, etc. Regardless of the cross-sectional shape of the aperture 52, it should have a minimum dimension or diameter of at least about 0.2 inches. Desirably, the aperture 52 has a minimum cross-section dimension or diameter of from between about 0.2 inches to about 2 inches. More desirably, the aperture 52 has a minimum cross-section dimension or diameter of from between about 0.3 inches to about 1.5 inches. Even more desirably, the aperture 52 has a minimum cross-section dimension or diameter of from between about 0.4 inches to about 1.25 inches.

Still referring to FIG. 8, the attachment member 38 further has a tightening device 54 which interacts with the aperture 52. The tightening device 54 is depicted as a threaded shaft 56 having a first end 58 and a second end 60. The threaded shaft 56 is sized and configured to engage with a threaded hole 62. Positioned on the first end 58 of the threaded shaft 56 is a knob 64 having a through bore (not shown) formed therethrough. The knob 64 houses a handle 66. The handle 66 is aligned at an angle to the threaded shaft 56. In FIG. 8, the handle 66 is shown being aligned perpendicular to the threaded shaft 56. The handle 66 has a first enlarged end 68 and a second enlarged end 70 which prevent the handle from separating from the knob 64. The first and second enlarged ends, 68 and 70 respectively, can be treaded onto the handle 66 so as to be removable, if desired.

By turning the handle 66 in a first direction, for example clockwise, one can advance the threaded shaft 56 into the aperture 52 and by turning the handle 66 in an opposite direction, for example counterclockwise; one can withdraw the threaded shaft 56 from the aperture 52.

Referring now to FIGS. 1 and 9-11, the anterior support device 14 includes an elongated member 72 having a distal end 74 and a threaded end 75. The elongated member 72 is sized and configured such that the distal end 74 can be inserted into the aperture 52. The elongated member 72 is capable of being retained in a predetermined position by the tightening device 54. The elongated member 72 is shown having a hexagonal cross-section but can have any geometrically shaped cross-section one desires. It is also possible to machine the cross section of the aperture 52 to be similar in shape to the cross section of the elongated member 72, just slightly larger. By making both the aperture 52 and the elongated member 72 to the same geometrical configuration, for example, both being hexagonal, one can prevent the elongated member 72 from rotating within the aperture 52.

Figures 9, 10, 11:
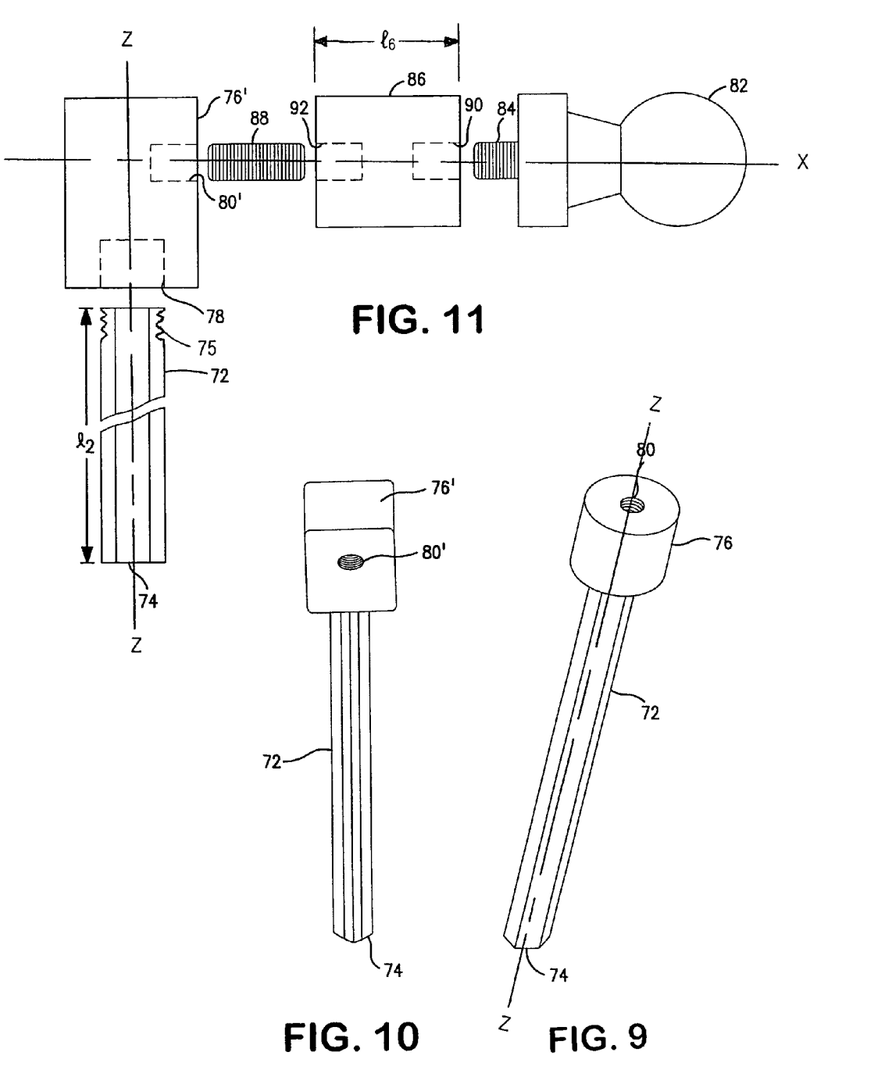
FIG. 9 is a perspective view of an elongated member secured to an adapter having a vertically aligned threaded bore formed therein to which a first pivotable connector is attached.
FIG. 10 is a perspective view of an elongated member secured to an adapter having a first threaded bore formed therein and a second threaded bore formed at a right angle to said first threaded bore, the second threaded bore capable of having a first pivotable connector attached thereto.
FIG. 11 is an exploded view of an elongated member, the adapter shown in FIG. 10, a threaded stud, a sleeve and a first pivotable connector attachable to said sleeve.

In FIG. 11, the elongated member 72 is shown having a length $l_2$ between the distal end 74 and the threaded end 75. The length $l_2$ can vary in dimension. Typically, the length $l_2$ of the elongated member 72 is between about 2 inches to about 24 inches. Desirably, the length $l_2$ of the elongated member 72 ranges from between about 3 inches to about 18 inches. More desirably, the length $l_2$ of the elongated member 72 ranges from between about 4 inches to about 12 inches. Even more desirably, the length $l_2$ of the elongated member 72 is at least about 6 inches. The length $l_2$ of the elongated member 72 will permit the anterior support device 14 to be raised or lowered with respect to the major surface 16 or 16' of the treatment device 12 or 12' so as to partially support the torso of people of varying height.

Once the distal end 74 of the elongated member 72 is inserted or positioned in the aperture 52 of one of the attachment members 38, the elongated member 72 can be locked in place by turning the handle 66 in a first direction, for example clockwise. This action will cause the tightening device 54 to advance the threaded shaft 56 into contact with the elongated member 72 and maintain the elongated member 72 at a desired vertical height within the aperture 52. Since the aperture 52 is located in the second body member 46, the angular orientation of the elongated member 72 can be changed as the second body member 46 is rotated relative to the first body member 44 of the attachment member 38. The elongated member 72 can be angled or positioned from between 0 to 180 degrees relative to the vertical central axis Z-Z. Desirably, the elongated member 72 is aligned parallel to the vertical central axis Z-Z.

Still referring to FIGS. 1 and 9, the anterior support device 14 also includes an adapter 76 which contains a first threaded bore 78 and a second threaded bore 80. The first threaded bore 78 is visible only in FIG. 1. The first and second threaded bores, 78 and 80 respectively, are axially aligned with the vertical central axis Z-Z. The first and second threaded bores, 78 and 80 respectively, are coaxially axially aligned to one another. As shown, the first and second threaded bores, 78 and 80 respectively, share the same axis Z-Z. The threaded end 75 of the elongated member 72 is sized and configured to mate with the threads of the first threaded bore 78.

In FIGS. 10 and 11, an alternative design of an adapter 76' is shown. The adapter 76' contains a first threaded bore 78 (visible in FIG. 11) and a second threaded bore 80'. In this embodiment, the first threaded bore 78 is axially aligned with the vertical central axis Z-Z while the second threaded bore 80' is arranged at a right angle to the first threaded bore 78. As depicted in FIG. 11, the second threaded bore 80' is aligned with the longitudinal central axis X-X. The threaded end 75 of the elongated member 72 can be size and configured to mate with the threads of the first threaded bore 78. The second threaded bore 80' is sized and configured to mate with either a threaded stud 84, which is secured to the first pivotable connector 82, or to a separate threaded stud 88.

Referring to FIGS. 1 and 11, a first pivotable connector 82 is directly or indirectly secured to one of the adapters 76 or 76'. The first pivotable connector 82 can be a ball joint, as shown. Alternatively, the first pivotable connector 82 can be a ball swivel or be some other type of device known to those skilled in the art which will permit pivotable motion. In FIG. 1, the first pivotable connector 82 is directly attached to the adapter 76 by a threaded stud 84. In FIG. 11, the first pivotable connector 82 is indirectly attached to the adapter 76 via a sleeve 86 and a threaded stud 88. The sleeve 86 is shown having a first threaded bore 90 and a second threaded bore 92. The first and second threaded bores, 90 and 92 respectively, are coaxially aligned along the longitudinal axis X-X. In this embodiment, the first threaded bore 90 is separate and distinct from the second threaded bore 92. The first pivotable connector 82 is attached to the sleeve 86 by threading the threaded stud 84 into the first threaded bore 90. In turn, the threaded stud 88 can be threaded into the second threaded bore 92 as well as being threaded into the threaded bore 80' formed in the adapter 76' This action will secure the first pivotable connector 82 to the sleeve 86 and the sleeve 86 to the adapter 76'. The primary purpose of the sleeve 86 is to space the first pivotable connector 82 farther away from the adapter 76'. In certain situations, it is advantageous to utilize the sleeve 86 especially when the adapter 76' has first and second threaded bores 78 and 80' that are not coaxially aligned to one another.

Figure 12:
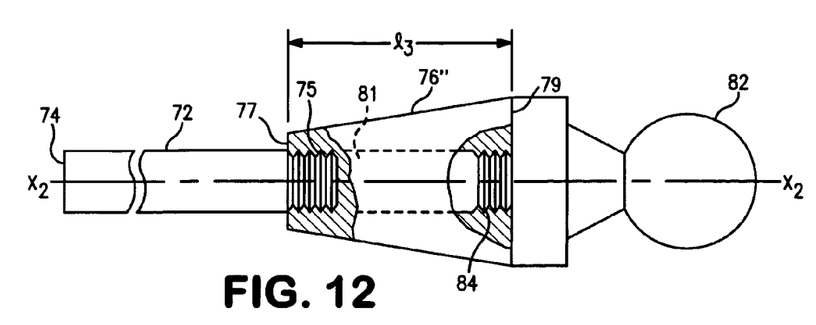
FIG. 12 is a partial cut away side view of an alternative embodiment of a trapezoidal shaped adapter having a single threaded through bore formed therein to which both the elongated member and the first pivotable connector is attached.
Figure 13:
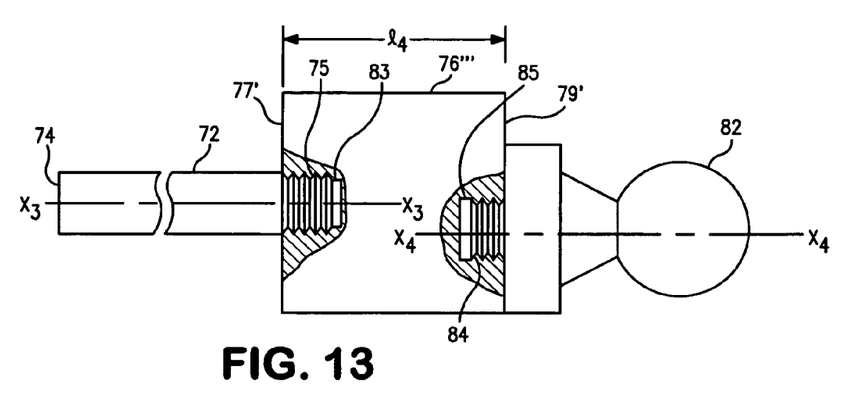
FIG. 13 is a partial cut away side view of still another embodiment of an adapter having first and second bores which are axially misaligned to which the elongated member and the first pivotable connector are attached.
Figure 14:
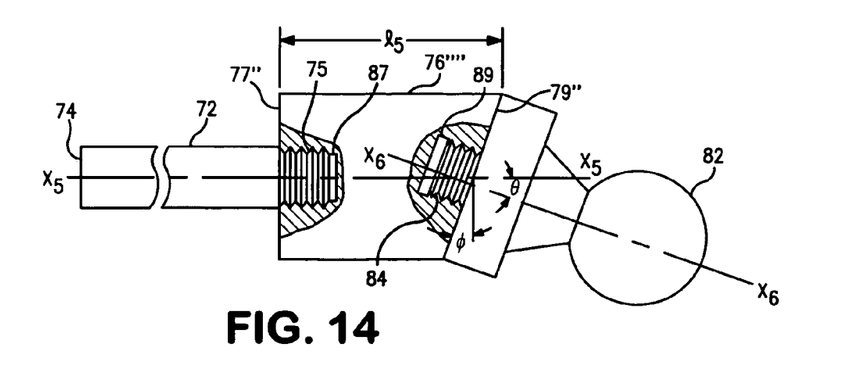
FIG. 14 is a partial cut away side view of still another embodiment of an adapter having a first end wall aligned at an angle to a second end wall and having first and second bores which are perpendicularly aligned with said first and second end walls, respectively, to which the elongated member and the first pivotable connector are attached.

Referring now to FIGS. 12-14, three alternative embodiments of an adapter 76", 76'" and 76"" are depicted. In FIG. 12, the adapter 76" is conical or trapezoidal in shape. The adapter 76" has a first end 77 and a spaced apart second end 79. The first end 77 is smaller in dimension than the second end 79. Stated another way, the second end 79 is larger than the first end 77. The adapter 76" has a length $l_3$ measured between the first and second ends, 77 and 79 respectively. The adapter 76" has a single threaded bore 81 formed therethrough which is aligned along a longitudinal central axis $X_2$-$X_2$. The single threaded bore 81 extends completely through the length of the adapter 76" from the first end 77 to the second end 79. The threaded end 75 of the elongated member 72 is sized and configured to mate with the threaded bore 81 approximate the first end 77. The first pivotable connector 82, which is desirably a ball joint, is sized and configured to mate with the second end 79 of the adapter 76".

As explained above, the first pivotable connector 82 has a threaded stud 84 secured thereto. The threaded stud 84 is sized and configured to mate with the single threaded bore 81 approximate the second end 79. Since the threads on both the threaded end 75 and on the threaded stud 84 are being threaded into the single threaded bore 81, the formation of the threads on the threaded end 75 have to be formed opposite to the threads formed on the threaded stud 84. For example, the threads on the threaded end 75 can be right hand threads while the threads on the threaded stud 84 are left hand threads. Alternatively, the threads on the threaded end 75 can be left hand threads while the threads on the threaded stud 84 are right hand threads.

In FIG. 11, since the threaded bores 78 and 80' are separate and distinct bores that do not extend completely through the adapter 76'. Therefore the threads formed on the threaded end 75 and on the threaded stud 88 can both be either right hand or left hand threads. Alternatively, the threads on the threaded end 75 can be right hand threads and the threads on the threaded stud 88 can be left hand threads.

Turning to FIG. 13 another adapter 76'" is shown which can vary in shape. The adapter 76'" can be of a cylindrical shape with a circular cross-section, be a block having a square or rectangular cross-section, or be of some other geometrical configuration having any desired cross-sectional shape. The adapter 76'" has a first end 77' and a spaced apart second end 79'. The first end 77' is approximately the same size and configuration as the second end 79'. The adapter 76'" has a length $l_4$ measured between the first and second ends, 77' and 79' respectively. The adapter 76'" has a first threaded bore 83 and a second threaded bore 85 formed therein. The first threaded bore 83 is aligned with a longitudinal axis $X_3$-$X_3$ and is formed in the first end 77'. The second threaded bore 85 is aligned with a longitudinal axis $X_4$-$X_4$ and is formed in the second end 79'. The longitudinal axis $X_3$-$X_3$ is aligned parallel to and is offset from the longitudinal axis $X_4$-$X_4$. Therefore, the first threaded bore 83 is coaxially aligned with the second threaded bore 85. The offset can vary in dimension. The offset can range from between 0.1 inches to 2 inches. Desirably, the offset is less than 1 inch.

Each of the first and second threaded bores, 83 or 85 respectively, extends partially into the adapter 76'". The amount that each of the first and second threaded bores, 83 and 85 respectively, extends into the adapter 76'" can vary. Desirably, each of the first and second threaded bores, 83 and 85 respectively, extends into the adapter 76'" a distance of at least 0.25 inches. More desirably, each of the first and second threaded bores, 83 and 85 respectively, extends into the adapter 76'" a distance of from between about 0.25 inches to about 1 inch. The threaded end 75 of the elongated member 72 is sized and configured to mate with the first threaded bore 83 and the threaded stud 84 is sized and configured to mate with the second threaded bore 85. The adapter 76'" allows the first pivotable connector 82 to be offset from the elongated member 72. This feature permits the anterior support device 14 to be more versatile and experience a greater degree of travel. It is believed that this is the first time that the structure of the adapter 76'" has been utilized in an anterior support device 14 to obtain greater flexibility in the degree of travel.

Turning now to FIG. 14, still another adapter 76"" is shown which can vary in shape. The adapter 76"" can be of a cylindrical shape with a circular cross-section, be a block having a square or rectangular cross-section, or be of some other geometrical configuration having any desired cross-sectional shape. The adapter 76"" has a first end 77" and a spaced apart second end 79". The adapter 76"" has a length $l_5$ measured between the first and second ends, 77" and 79" respectively. The first end 77" is equal to or slightly smaller than the second end 79". Alternatively, the first end 77" can be larger than the second end 79". In addition, the first and second ends, 77" and 79" respectively, are aligned at an angle phi $\varnothing$ to one another. The angle $\varnothing$ can range from between about 1 degree to about 30 degrees. Desirably, the angle $\varnothing$ ranges from between about 1 degrees to about 15 degrees. More desirably, the angle $\varnothing$ ranges from between about 2 degrees to about 10 degrees.

Even more desirably, the angle Ø ranges from between about 3 degrees to about 10 degrees.

The adapter 76'''' has a first threaded bore 87 and a second threaded bore 89 formed therein. The first threaded bore 87 is aligned with a longitudinal axis $X_5$-$X_5$ and is formed in the first end 77''. The second threaded bore 89 is aligned with a longitudinal axis $X_6$-$X_6$ and is formed in the second end 79''. By angling the second end 79'' relative to the first end 77'', the adapter 76'''' can be more versatile and the anterior support device 14 can experience a greater degree of travel. It is believed that this is the first time that the structure of the adapter 76'''' has been utilized in an anterior support device 14 to obtain greater flexibility in the degree of travel.

The first pivotable connector 82 is aligned at an angle theta θ to the longitudinal axis $X_5$-$X_5$. The angle θ should be equal to the angle Ø. The angle θ can range from between about 1 degree to about 30 degrees. Desirably, the angle θ ranges from between about 1 degrees to about 15 degrees. More desirably, the angle θ ranges from between about 2 degrees to about 10 degrees. Even more desirably, the angle θ ranges from between about 3 degrees to about 10 degrees.

It should be understood that one or more sleeves 86, as shown in FIG. 11, can be utilized so as to space the first pivotable connector 82 farther away from any of the adapters 76'', 76''' and 76''''. The sleeve 86 has a length $l_6$ which can vary in dimension. Desirably, the length $l_6$ of the sleeve 86 is at least about 0.5 inches. More desirably, the length $l_6$ of the sleeve 86 is at least about 1 inch. Even more desirably, the length $l_6$ of the sleeve 86 is from between about 2 inches to about 6 inches.

Figure 15:
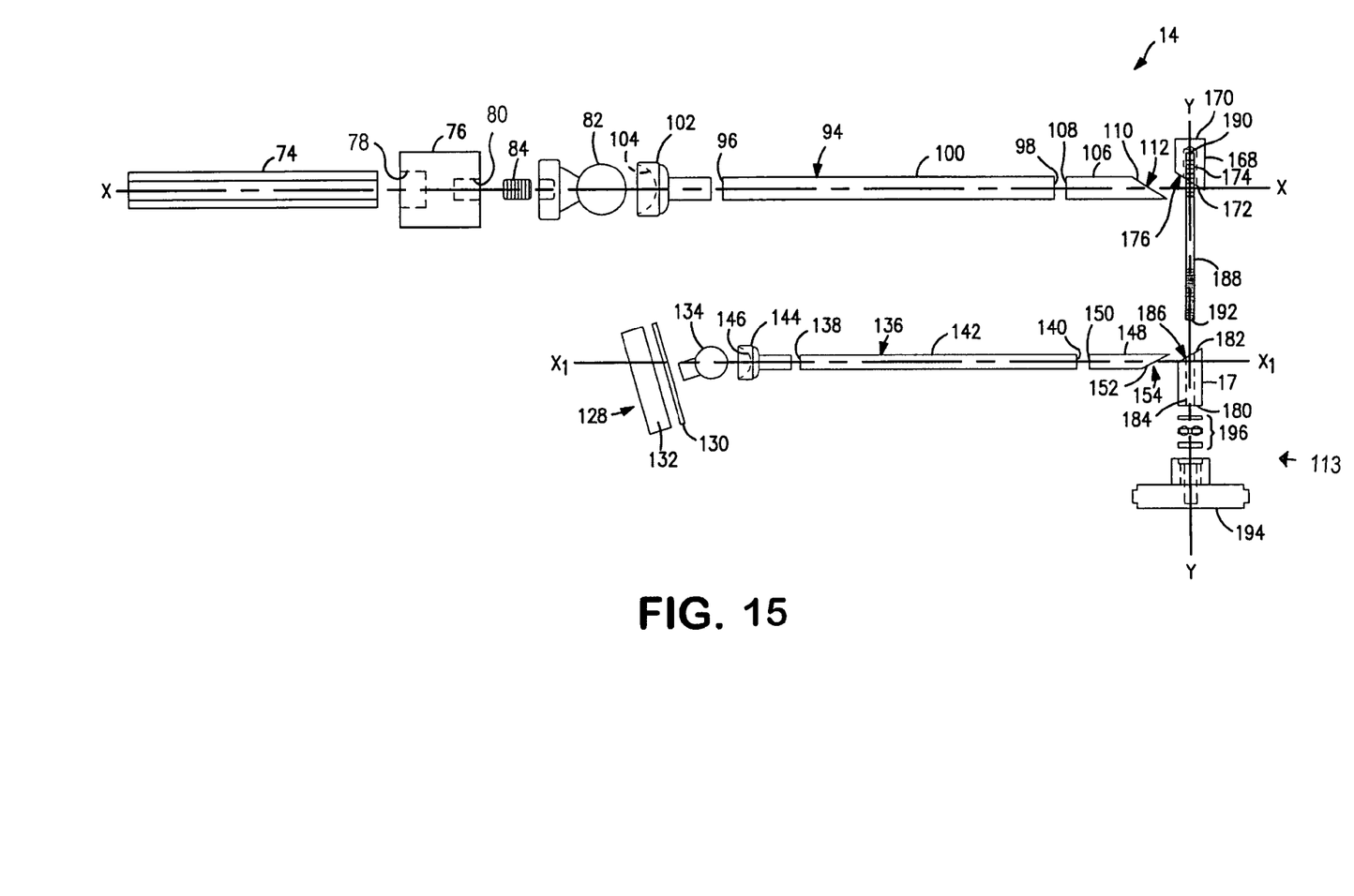
FIG. 15 is an exploded view of the components of one of the anterior support devices shown in FIG. 1.
Figure 16:
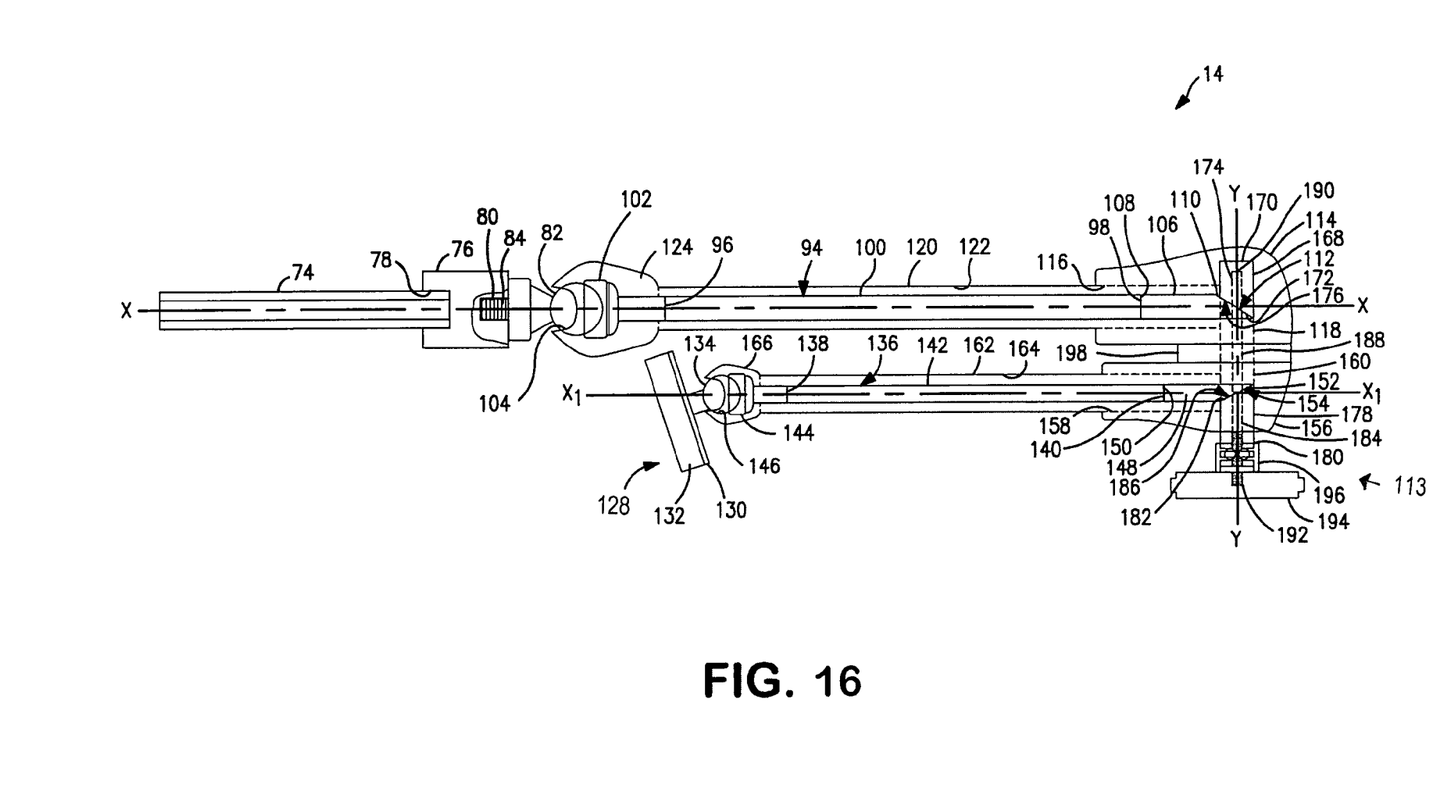
FIG. 16 is an assembled view of the components of one of the anterior support devices shown in FIG. 1 with the adapter partially broken away to show the fastener.

Referring now to FIGS. 15 and 16, the anterior support device 14 further includes a first movable rod 94 having a first end 96 and a second end 98. Desirably, the first movable rod 94 is an elongated cylindrical rod having a uniform outside diameter 100. However, the first movable rod 94 could be formed with any desired geometrically shaped cross-section, including but not limited to: a triangle, a square, a rectangle, a hexagon, a circle, an oval, etc.

A first friction cup 102 is positioned adjacent to the first end 96 of the first movable rod 94. The first friction cup 102 is capable of engaging the first pivotable connector 82 so as to provide pivoting movement thereabout when urged into tight contact with the first pivotable connector 82 by movement of the first movable rod 94. The first friction cup 102 can be held in position on the first pivotable connector 82 by a retainer ring, not shown, if needed. It should also be noted that the first friction cup 102 has a concave surface 104 which is sized and shaped to mate with a portion of the outer periphery of the first pivotable connector 82.

The anterior support device 14 also includes an actuating mechanism 113 connected to the first and second movable rods, 94 and 136 respectively. The actuating mechanism 113 enables the first and second movable rods, 94 and 136 respectively, to be locked in a set position to maintain the padded rest 128 in a desired orientation relative to the treatment device 12. The actuating mechanism 113 includes a first connecting member 106. The first connecting member 106 has a first end 108 and a second end 110. The first connecting member 106 shares a common central axis X-X with the first movable rod 94. The first end 108 of the first connecting member 106 is positioned adjacent to the second end 98 of the first movable rod 94 and the second end 110 of the first connecting member 106 has an angled surface 112. The angled surface 112 can be formed at an angle of from between about 15 degrees to about 75 degrees relative to the central axis X-X. More desirably, the angled surface 112 can be formed at an angle of from between about 30 degrees to about 60 degrees relative to the central axis X-X. Even more desirably, the angled surface 112 can be formed at an angle of from between about 35 degrees to about 55 degrees relative to the central axis X-X. Most desirably, the angled surface 112 can be formed at an angle of about 45 degrees relative to the central axis X-X.

Referring to FIG. 16, the actuating mechanism 113 also includes a first elbow 114 having a first bore 116 and a second bore 118 formed therein. The first and second bores, 116 and 118 respectively, are aligned at an angle to one another. The angle can be any number of degrees from between about 1 degree to about 90 degrees. Desirably, the angle is from between about 45 degrees to about 90 degrees. More desirably, the angle is a right angle of 90 degrees. The first bore 116 is of sufficient size to receive the first connecting member 106.

The anterior support device 14 further includes an exterior tube 120 which encloses the first movable rod 94. The exterior tube 120 has an inner diameter 122 which is sized to be slightly larger than the outside diameter 100 of the first movable rod 94. For example, inner diameter 122 of the exterior tube 120 can range in sized from between about 0.005 inches to about 0.01 inches larger than the outside diameter 100 of the first movable rod 94. By machining to close tolerances and/or by using silicone, dry grease or other lubricant, one can eliminate the need for bearings.

The anterior support device 14 also has a hollow cap 124 which covers the first pivotable connector 82 and the first friction cup 102. The hollow cap 124 is first positioned in place over the first pivotable connector 82 and the first friction cup 102 and then the exterior tube 120 is slid over the first movable rod 94. The opposite end of the exterior tube 120 is sized to fit snuggly in the first bore 116 formed in the first elbow 114. It should be noted that the hollow cap 124, the exterior tube 120 and the first elbow 114, when assembled, will not change in length.

Still referring to FIGS. 15 and 16, the anterior support device 14 further includes a padded rest 128. The padded rest 128 includes a back plate 130 and a padded or cushioned member 132 secured to the back plate 130. The padded or cushioned member 132 can be constructed from various materials, including but not limited to: foam, closed cell foam, open cell foam, cotton, polyurethane, soft plastic, tow, broken flax or hemp, any natural or synthetic fibers, etc. The padded or cushioned member 132 can be secured to the back plate 130 by means known to those skilled in the art, including but not limited to: sewing, by adhesive, by glue, by a mechanical connection, by a chemical connection, etc.

The anterior support device 14 also includes a second pivotable connector 134 secured to the back plate 130 of the padded rest 128. The second pivotable connector 134 can be attached to the back plate 130 in a similar fashion as was used to secure the first pivotable connector 82 to the adapter 76. Alternatively, the second pivotable connector 134 could be welded to the back plate 130.

The anterior support device 14 also includes a second movable rod 136 having a first end 138, a second end 140 and an outside diameter 142. Desirably, the second movable rod 136 is an elongated cylindrical rod having a uniform outside diameter 142. However, the second movable rod 136 could be formed with any desired geometrically shaped cross-section, including but not limited to: a triangle, a square, a rectangle, a hexagon, a circle, an oval, etc.

A second friction cup 144 is positioned adjacent to the first end 138 of the second movable rod 136. The second friction cup 144 is capable of engaging the second pivotable connector 134 so as to provide pivoting movement thereabout when urged into tight contact with the second pivotable connector 134 by movement of the second movable rod 136. The second friction cup 14 can be held in position on the second pivotable connector 134 by a retainer ring, not shown, if needed. It should also be noted that the second friction cup 144 has a concave surface 146 which is sized and shaped to mate with a portion of the outer periphery of the second pivotable connector 134.

The actuating mechanism 113 further includes a second connecting member 148 having a first end 150 and a second end 152. The second connecting member 148 shares a common central axis $X_1$-$X_1$ with the second movable rod 136. The first end 150 of the second connecting member 148 is positioned adjacent to the second end 140 of the second movable rod 136 and the second end 152 of the second connecting member 148 has an angled surface 154. The angled surface 154 can be formed at an angle of from between about 15 degrees to about 75 degrees relative to the central axis $X_1$-$X_1$. More desirably, the angled surface 154 can be formed at an angle of from between about 30 degrees to about 60 degrees relative to the central axis $X_1$-$X_1$. Even more desirably, the angled surface 154 can be formed at an angle of from between about 35 degrees to about 55 degrees relative to the central axis $X_1$-$X_1$. Most desirably, the angled surface 154 can be formed at an angle of about 45 degrees relative to the central axis $X_1$-$X_1$.

Referring again to FIG. 16, the anterior support device 14 also includes a second elbow 156 having a first bore 158 and a second bore 160 formed therein. The first and second bores, 158 and 160 respectively, are aligned at an angle to one another. The angle can be any number of degrees from between about 1 degree to about 905 degrees. Desirably, the angle is from between about 45 degrees to about 90 degrees. More desirably, the angle is a right angle of 90 degrees. The first bore 158 is of sufficient size to receive the second connecting member 148. The second bore 160 formed in the second elbow 156 is aligned with the second bore 118 formed in the first elbow 114 such that both of the second bores 118 and 160 have the same central axis Y-Y. The central axis Y-Y is arranged perpendicular to the central axes X-X and $X_1$-$X_1$.

The anterior support device 14 further includes an exterior tube 162 which encloses the second movable rod 136. The exterior tube 162 has an inner diameter 164 which is sized to be slightly larger than the outside diameter 142 of the second movable rod 136. For example, inner diameter 164 of the exterior tube 162 can range from between about 0.005 inches to about 0.01 inches larger than the outside diameter 142 of the second movable rod 136. By machining to close tolerances and/or by using silicone, dry grease or other lubricant, one can eliminate the need for bearings.

The anterior support device 14 also has a hollow cap 166 which covers the second pivotable connector 134 and second friction cup 144. The hollow cap 166 is first positioned in place over the second pivotable connector 134 and the second friction cup 144 and then the exterior tube 162 is slid over the second movable rod 136. The opposite end of the exterior tube 162 is sized to fit snuggly in the first bore 158 formed in the second elbow 156. It should be noted that the hollow cap 166, the exterior tube 162 and the second elbow 156, when assembled, will not change in length.

Referring again to FIGS. 15 and 16, the actuating mechanism 113 further includes a first block 168 having a first end 170 and a second end 172. The first block 168 is sized to snuggly fit into said second bore 118 formed in the first elbow 114. The first block 168 has a threaded bore 174 formed therein. The first block 168 is aligned at an angle to the first connecting member 106. Desirably, the first block 168 is aligned at a right angle to the first connecting member 106.

The threaded bore 174 is shown as a blind bore that does not extend completely through the first block 168. If desired, one could machine the threaded bore 174 completely through the first block 168. The second end 172 of the first block 168 has an angled surface 176 which is capable of engaging with the angled surface 112 of the first connecting member 106. The angled surface 176 can be formed at an angle of from between about 15 degrees to about 75 degrees relative to the central axis Y-Y. More desirably, the angled surface 176 can be formed at an angle of from between about 30 degrees to about 60 degrees relative to the central axis Y-Y. Even more desirably, the angled surface 176 can be formed at an angle of from between about 35 degrees to about 55 degrees relative to the central axis Y-Y. Most desirably, the angled surface 176 can be formed at an angle of about 45 degrees relative to the central axis Y-Y. The angle of the angled surface 176 of the first block 168 should be machined so that it mates with the angled surface 112 of the first connecting member 106.

The actuating mechanism 113 further includes a second block 178 having a first end 180 and a second end 182. The second block 178 is sized to snugly fit into the second bore 160 formed in the second elbow 156. The second block 178 has a threaded bore 184 formed completely therethrough. The second block 178 is aligned at an angle to the second connecting member 148. Desirably, the second block 178 is aligned at a right angle to the second connecting member 148. The second end 182 of the second block 178 has an angled surface 186 which is capable of engaging with of the angled surface 154 of the second connecting member 148.

Still referring to FIGS. 15 and 16, the actuating mechanism 113 further includes a threaded stem 188 extending completely through the second block 178 and into the first block 168. The threaded stem 188 has a first end 190 and a second end 192. The first end 190 of the threaded stem 188 enters the threaded bore 174 formed in the first block 168 and terminates within this threaded bore 174. The second end 192 of the threaded stem 188 extends completely through the threaded bore 184 formed in the second block 178 and extends outward from the second elbow 156. A rotatable knob 194 is secured to the second end 192 of the threaded stem 188. As the knob 194 is rotated in a first direction, for example in a clockwise direction, the threaded stem 188 draws the angled surface 176 of the first block 168 against the angled surface 112 of the first connecting member 106 and draws the angled surface 186 of the second block 178 against the angled surface 154 of the second connecting member 148. This causes the first and second movable rods, 94 and 136 respectively, to move to the left in FIGS. 15 and 16 and push the first and second friction cups, 102 and 144 respectively, also to the left. This in turn causes the first and second friction cups, 102 and 144 respectively, to lock against the first and second pivotable connectors, 82 and 136 respectively. In doing so, the padded rest 128 is locked in a desired orientation relative to the treatment device 12.

The actuating mechanism 113 can also include a roller, a bearing or bearing assembly 196 positioned between the first end 180 of the second block 178 and the rotatable knob 194. The roller, bearing or bearing assembly 196 allows the knob 194 to rotate in a smooth fashion relative to the second block 178. As stated above, the knob 194 can be rotated clockwise to tighten the connections between the first connecting member 106 and the first block 168 and the connection between the second connecting member 148 and the second block 178. As the knob 194 is progressively turned clockwise, the connections are tightened and this causes the first movable rod 94 to move to the left and causes the first friction cup 102 to engage tightly with the first pivotable connector 82. Simultaneously, the second movable rod 136 will also move to the left and cause the second friction cup 144 to engage tightly with the second pivotable connector 134. Accordingly, by tightening the single knob 194, the user of the anterior support device 14 can lock the various components in a set position. When the user of the anterior support device 14 wishes to move the padded rest 128 to a different orientation, he or she simply rotates the knob 194 in a counter clockwise direction and this action loosens the engagement between the first connecting member 106 and the first block 168 and the engagement between the second connecting member 148 and the second block 178. As this occurs, the first movable rod 94 moves to the right and the engagement between the first friction cup 102 and the first pivotable connector 82 is relaxed. Simultaneously, the second movable rod 136 also moves to the right and the engagement between the second friction cup 144 and the second pivotable connector 134 is relaxed. The user can reposition the padded rest 128 and then tighten the knob 194 as described above.

Again referring to FIG. 16, the actuating mechanism 113 can further include a friction disc 198 positioned between the first and second elbows, 114 and 156 respectively. The friction disc 198 can facilitate rotation between the first and second elbows, 114 and 156 respectively, in a smooth fashion. The friction disc 198 can be constructed out of various materials known to those skilled in the art. Desirably, the friction disc 198 is formed from a material having smooth surfaces. The material can be hard or soft. Examples of materials that can be used to construct the friction disc 198 include but are not limited to: plastic, rubber, metal, foam, hard cell foams, graphite, etc.

Still referring to FIGS. 15 and 16, the actuating mechanism 113 connects the first and second movable rods, 94 and 136 respectively, together and enables the first and second movable rods, 94 and 136 respectively, to be locked in a set position to maintain the padded rest 128 in a desired orientation relative to the treatment device 12 or 12'. The actuating mechanism 113 includes a first connecting member 106 having a first end 108 and an angled second end 112. The actuating mechanism 113 also includes a first block 168 positioned at an angle to the first connecting member 106 which has a first end 170 and an angled second end 172. The angled second end 112 of the first connecting member 106 contacts the angled second end 172 of the first block 168. The actuating mechanism 113 also has a second connecting member 148 having a first end 150 and an angled second end 154. The actuating mechanism 113 further includes a second block 178 positioned at an angle to the second connecting member 148 which has a first end 150 and an angled second end 152. The angled second end 152 of the second connecting member 148 contacts the angled second end 182 of the second block 178. The first and second blocks, 168 and 178 respectively, are aligned along a common axis Y-Y. The first block 168 has a threaded bore 174 formed therein and the second block 178 has a threaded bore 184 formed therethrough. The actuating mechanism 113 further includes a threaded stem 188 having a first end 190 and a second end 192. The first end 190 of the threaded stem 188 extends through the second block 178 and is threaded into the first block 168. A knob 194 is secured to the second end 192 of the threaded stem 188. The knob 194 is capable of rotating the threaded stem 188 in a clockwise direction to cause the angled second ends 172 and 182 of the first and second blocks, 168 and 178 respectively, to engage with the angled second ends 112 and 154 of the first and second connecting members, 94 and 136 respectively, and move the first and second friction cups, 102 and 144 respectively, so that the first and second friction cups, 102 and 144 respectively, will form a tight connection with the first and second pivotable connectors, 82 and 134 respectively. This action will permit the padded rest 128 to be locked in a desired position. The knob 194 is also capable of rotating the threaded stem 188 in a counterclockwise direction to cause the angled second ends 172 and 182 of the first and second blocks, 168 and 178 respectively, to move away from the angled second ends 112 and 154 of the first and second connecting members, 106 and 148 respectively, and allow the first and second friction cups, 102 and 144 respectively, to move away from the first and second pivotable connectors, 82 and 134 respectively. This action will allow loosening of the lock between the first and second friction cups, 102 and 144 respectively, and the first and second pivotable connectors, 82 and 134 respectively.

Returning to FIG. 1, the combination 10 is illustrated with two attachment members 38 both movably positioned along a single rail 30. Each attachment member 38 has an aperture 52 through which can be inserted an elongated member 72 of an anterior support device 14. The tightening device 54 associated with each attachment member 38 can be used to securely fasten the elongated member 72 at a desired height relative to the major surface 16 or 16' of the treatment device 12 or 12' respectively.

While the invention has been described in conjunction with several specific embodiments, it is to be understood that many alternatives, modifications and variations will be apparent to those skilled in the art in light of the foregoing description. Accordingly, this invention is intended to embrace all such alternatives, modifications and variations which fall within the spirit and scope of the appended claims.

We claim:

1. A combination comprising:
a) a treatment device having a flat major surface, a length, first and second edges extending parallel to said length, and a pair of rails each secured to one of said first and second edges;
b) an attachment member movably secured to at least one of said first and second rails, said attachment member having an aperture formed therethrough and a tightening device which interacts with said aperture; and
c) an anterior support device having an elongated member sized and configured to be inserted into said aperture and capable of being retained in a predetermined position by said tightening device, said elongated member having a threaded end, an adapter having a first threaded bore and a second threaded bore formed therein, said threaded end of said elongated member being threaded into said first threaded bore of said adapter, a first pivotable connector having a threaded stud which is threaded into said second threaded bore of said adapter, a first movable rod having a first end and a second end, said first end of said first movable rod having a friction cup formed thereon which engages with said first pivotable connector and is capable of pivoting thereabout, said anterior support device further including a padded rest against which a user can lean his torso for support, a second pivotable connector secured to said padded rest, and a second movable rod having a first end and a second end, said first end of said second pivotable connector having a friction cup formed thereon which engages said second pivotable connector and is capable of pivoting thereabout, and an actuating mechanism connecting said first and second movable rods together and which enables said first and second movable rods to be locked in a set position to maintain said padded rest in a desired orientation relative to said treatment device, said actuating mechanism including a first connecting member having a first end and an angled second end, a first block positioned at an angle to said first connecting member and having a first end and an angled second end, said angled second end of said first connecting member contacting said angled second end of said first block, a second connecting member having a first end and an angled second end, a second block positioned at an angle to said second connecting member and having a first end and an angled second end, said angled second end of said second connecting member contacting said angled second end of said second block, said first and second blocks being aligned along a common axis, said first block having a threaded bore formed therein and said second block having a threaded bore formed therethrough, a threaded stem having a first end and a second end, said first end of said threaded stem extending through said second block and being threaded into said first block, and a knob secured to said second end of said threaded stem, said knob capable of rotating said threaded stem in a clockwise direction to cause said angled second ends of said first and second blocks, respectively, to engage with said angled second ends of said first and second connecting members, respectively, and move said first and second friction cups, respectively, so that said first and second friction cups will form a tight connection with said first and second pivotable connectors, respectively, to permit said padded rest to be locked in a desired position, and said knob capable of rotating said threaded stem in a counterclockwise direction to cause said angled second ends of said first and second blocks to move away from said angled second ends of said first and second connecting members, respectively, and allow said first and second friction cups to move away from said first and second pivotable connectors, respectively, thereby loosening said lock between said first and second friction cups and said first and second pivotable connectors, respectively.

2. The combination of claim 1 wherein said adapter has a length measured between said first and second ends, and said first threaded bore formed in said adapter extends inward from said first end and said second threaded bore formed in said adapter extends inward from said second end, and said first threaded bore is coaxially aligned with said second threaded bore.

3. The combination of claim 2 wherein said first threaded bore and said second threaded bore are aligned parallel to one another and are offset from one another.

4. The combination of claim 1 wherein said threaded end of said elongated member is a right handed thread and said threaded stud of said first pivotable connector is a right handed thread, and said first pivotable connector is a ball joint.

5. The combination of claim 1 wherein said adapter has a length, and said first threaded bore formed therein extends inward from said first end and said second threaded bore formed therein extends inward from said second end, said first threaded bore being aligned on a first axis and said second threaded bore being aligned on a second axis, said first and second axes being aligned parallel to and offset from one another, and said threaded end of said elongated member is threaded into said first bore and said threaded stud of said first pivotable connector is threaded into said second bore.

6. The combination of claim 1 wherein said adapter has a length and said first end of said adapter is aligned at an angle Ø to said second end of said adapter, and said angle Ø ranges from between about 1 degree to about 15 degrees.

7. The combination of claim 6 wherein said angle Ø ranges from between about 2 degrees to about 10 degrees.

8. The combination of claim 1 wherein said aperture formed in said attachment member has an elliptical cross-section with a minimum dimension of at least about 0.2 inches.

9. The combination of claim 1 wherein said elongated member has a hexagonal cross-section and a length ranging from between about 2 inches to 24 inches.

10. A combination comprising:
a) a treatment device having a flat major surface, a length, first and second edges extending parallel to said length, and a pair of rails each secured to one of said first and second edges;
b) an attachment member movably secured to at least one of said first and second rails, said attachment member having an aperture formed therethrough and a tightening device which interacts with said aperture; and
c) an anterior support device having an elongated member sized and configured to be inserted into said aperture and capable of being retained in a predetermined position by said tightening device, said elongated member having a threaded end, an adapter having a first end, a second end and a length therebetween, said adapter having a single threaded bore formed therethrough, said threaded end of said elongated member being threaded into said single threaded bore adjacent to said first end, a first pivotable connector having a threaded stud which is threaded into said single threaded bore adjacent to said second end, a first movable rod having a first end and a second end, said first end of said first movable rod having a friction cup formed thereon which engages with said first pivotable connector and is capable of pivoting thereabout, said anterior support device further including a padded rest against which a user can lean his torso for support, a second pivotable connector secured to said padded rest, and a second movable rod having a first end and a second end, said first end of said second movable rod having a friction cup formed thereon which engages said second pivotable connector and is capable of pivoting thereabout, and an actuating mechanism connecting said first and second movable rods together and which enables said first and second movable rods to be locked in a set position to maintain said padded rest in a desired orientation relative to said treatment device, said actuating mechanism including a first connecting member having a first end and an angled second end, a first block positioned at an angle to said first connecting member and having a first end and an angled second end, said angled second end of said first connecting member contacting said angled second end of said first block, a second connecting member having a first end and an angled second end, a second block positioned at an angle to said second connecting member and having a first end and an angled second end, said angled second end of said second connecting member contacting said angled second end of said second block, said first and second blocks being aligned along a common axis, said first block having a threaded bore formed therein and said second block having a threaded bore formed therethrough, a threaded stem having a first end and a second end, said first end of said threaded stem extending through said second block and being threaded into said first block, and a knob secured to said second end of said threaded stem, said knob capable of rotating said threaded stem in a clockwise direction to cause said angled second ends of said first and second blocks, respectively, to engage with said angled second ends of said first and second connecting members, respectively, and move said first and second friction cups, respectively, so that said first and second friction cups will form a tight connection with said first and second pivotable connectors, respectively, to permit said padded rest to be locked in a desired position, and said knob capable of rotating said threaded stem in a counterclockwise direction to cause said angled second ends of said first and second blocks to move away from said angled second ends of said first and second connecting members, respectively, and allow said first and second friction cups to move away from said first and second pivotable connectors, respectively, thereby loosening said lock between said first and second friction cups and said first and second pivotable connectors, respectively.

11. The combination of claim 10 further comprising a second attachment member movable along a second of said pair of rails, said second attachment member capable of being secured to said rail in a desired position, and said second attachment member having an aperture formed therethrough and a tightening device which interacts with said aperture.

12. The combination of claim 10 further comprising a second attachment member movable along and capable of being secured to said same rail that said first attachment member is secured to, and said second attachment member having an aperture formed therethrough and a tightening device which interacts with said aperture.

13. The combination of claim 10 wherein said treatment device has a pair of ends and said pair of rails extends beyond each of said pair of ends.

14. The combination of claim 10 wherein said threaded end of said elongated member is a right handed thread which is threaded into said single threaded bore adjacent to said first end of said adapter, and first pivotable connector is a ball joint having a threaded stud with a left handed thread which is threaded into said single threaded bore adjacent to said second end of said adapter.

15. The combination of claim 10 wherein said first block is aligned at a right angle to said first connecting member and said second block is aligned at a right angle to said second connecting member.

16. A combination which partially supports a person's torso, comprising:
a) a treatment device having a planar surface, a vertical central axis, a length, first and second edges extending parallel to said length, and a pair of rails each secured to one of said first and second edges and each of said pair of rails extending along a portion of said treatment device;
b) a first attachment member movably secured to at least one of said first and second rails, said first attachment member having an aperture formed therethrough and a tightening device which interacts with said aperture; and
c) an anterior support device having an elongated member sized and configured to be inserted into said aperture and capable of being retained in a predetermined position by said tightening device, said elongated member having a threaded end, an adapter having a first threaded bore and a second threaded bore formed therein, said threaded end of said elongated member being threaded into said first threaded bore of said adapter, a first pivotable connector having a threaded stud which is threaded into said second threaded bore of said adapter, a first movable rod having a first end and a second end, said first end of said first movable rod having a friction cup formed thereon which engages with said first pivotable connector and is capable of pivoting thereabout, said anterior support device further including a padded rest against which a user can lean his torso for support, a second pivotable connector secured to said padded rest, and a second movable rod having a first end and a second end, said first end of said second pivotable connector having a friction cup formed thereon which engages said second pivotable connector and is capable of pivoting thereabout, and an actuating mechanism connecting said first and second movable rods together and which enables said first and second movable rods to be locked in a set position to maintain said padded rest in a desired orientation relative to said treatment device, said actuating mechanism including a first connecting member having a first end and an angled second end, a first block positioned at a right angle to said first connecting member and having a first end and an angled second end, said angled second end of said first connecting member contacting said angled second end of said first block, a second connecting member having a first end and an angled second end, a second block positioned at a right angle to said second connecting member and having a first end and an angled second end, said angled second end of said second connecting member contacting said angled second end of said second block, said first and second blocks being aligned along a common axis, said first block having a threaded bore formed therein and said second block having a threaded bore formed therethrough, a threaded stem having a first end and a second end, said first end of said threaded stem extending through said second block and being threaded into said first block, and a knob secured to said second end of said threaded stem, said knob capable of rotating said threaded stem in a clockwise direction to cause said angled second ends of said first and second blocks, respectively, to engage with said angled second ends of said first and second connecting members, respectively, and move said first and second friction cups, respectively, so that said first and second friction cups will form a tight connection with said first and second pivotable connectors, respectively, to permit said padded rest to be locked in a desired position, and said knob capable of rotating said threaded stem in a counterclockwise direction to cause said angled second ends of said first and second blocks to move away from said angled second ends of said first and second connecting members, respectively, and allow said first and second friction cups to move away from said first and second pivotable connectors, respectively, thereby loosening said lock between said first and second friction cups and said first and second pivotable connectors, respectively.

17. The combination of claim 16 wherein said adapter has a length and said first end of said adapter is aligned at an angle Ø to said second end of said adapter, and said angle Ø ranges from between about 1 degree to about 15 degrees.

18. The combination of claim 17 wherein a sleeve is positioned between said adapter and said first pivotable connector, and said sleeve is secured to said second threaded bore of said adapter by a threaded stud.

19. The combination of claim 16 wherein said first threaded bore and said second threaded bore are aligned parallel to one another and are offset from one another.

20. The combination of claim 16 wherein said elongated member has a hexagonal cross-section and a length ranging from between about 3 inches to about 24 inches.

* * * * *